US010088406B2

(12) United States Patent
Cros et al.

(10) Patent No.: US 10,088,406 B2
(45) Date of Patent: Oct. 2, 2018

(54) METHOD AND DEVICE FOR MEASURING PERMEATION BY MASS SPECTROMETRY

(71) Applicant: COMMISSARIAT A L'ENERGIE ATOMIQUE ET AUX ENERGIES ALTERNATIVES, Paris (FR)

(72) Inventors: Stéphane Cros, Chambery (FR); Fabien Jaubert, Saint Egreve (FR); Arnaud Leroy, Chambery (FR); Christine Walsh, Clichy (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 94 days.

(21) Appl. No.: 14/948,485

(22) Filed: Nov. 23, 2015

(65) Prior Publication Data

US 2016/0146716 A1   May 26, 2016

(30) Foreign Application Priority Data

Nov. 24, 2014  (FR) ..................... 14 61342

(51) Int. Cl.
*G01N 15/08* (2006.01)
*G01N 27/62* (2006.01)

(52) U.S. Cl.
CPC ....... *G01N 15/082* (2013.01); *G01N 15/0826* (2013.01); *G01N 27/62* (2013.01); *G01N 2015/0846* (2013.01)

(58) Field of Classification Search
CPC ................................................ G01N 15/082
(Continued)

(56) References Cited

U.S. PATENT DOCUMENTS 5,131,261 A   7/1992   Tou et al.
5,265,463 A   11/1993  Loebig
(Continued)

FOREIGN PATENT DOCUMENTS

JP   S6361141 A    3/1988
WO   0233378 A1    4/2002
WO   02088657 A2   11/2002

OTHER PUBLICATIONS

Search Report for Application No. EP13176044 dated Dec. 2, 2013.
Preliminary Search Report for Application No. FR0601320 dated Sep. 14, 2006.

*Primary Examiner* — Manish S Shah
*Assistant Examiner* — Timothy Graves
(74) *Attorney, Agent, or Firm* — Lerner, David, Littenberg, Krumholz & Mentlik, LLP

(57) ABSTRACT

The invention relates to a method for measuring permeation of gases through a material comprising the following steps:
 a) Supplying gas to a permeation enclosure (10) during which a first chamber (11) is supplied with a target gas flow comprising at least one target gas corresponding to a gas for which one tries to determine the permeation through the material (M), and simultaneous supplying gas to a measurement enclosure (20) with at least one calibrated flow comprising at least one reference gas different from the target gas;
 b) during the gas supply step, measuring in the measurement enclosure (20) the reference gas present at instant (t) and the target gas present at the same instant (t) after having crossed the material (M) by permeation;
 c) calculating a correction factor at instant (t) by comparing the measurement of the reference gas present at instant (t) with the reference gas supply calibrated flow; and (Continued)

d) determining the permeation of the material (M) to said gas, from the measurement of the target gas present at instant (t) corrected with the correction factor at instant (t).

18 Claims, 3 Drawing Sheets

(58) Field of Classification Search
USPC .......................................................... 73/38
See application file for complete search history.

(56) References Cited

U.S. PATENT DOCUMENTS

| | | |
|---|---|---|
| 6,624,621 B2 | 9/2003 | North, Jr. |
| 2003/0001086 A1 | 1/2003 | Noerenberg et al. |
| 2003/0074954 A1 | 4/2003 | Engle et al. |
| 2004/0040372 A1 | 3/2004 | Plester et al. |
| 2004/0123646 A1 | 7/2004 | Echigo et al. |
| 2007/0259433 A1* | 11/2007 | Jones ............... G01N 33/241 436/31 |
| 2008/0060417 A1* | 3/2008 | DeRoos ............ G01N 15/0826 73/38 |
| 2008/0060418 A1* | 3/2008 | DeRoos ............ G01N 15/0826 73/38 |
| 2010/0223979 A1* | 9/2010 | Ploehn .............. G01N 15/0826 73/38 |
| 2014/0223999 A1* | 8/2014 | Graehlert .......... G01N 15/0826 73/38 |
| 2016/0202230 A1* | 7/2016 | Jones ................ G01N 33/241 73/38 |

\* cited by examiner

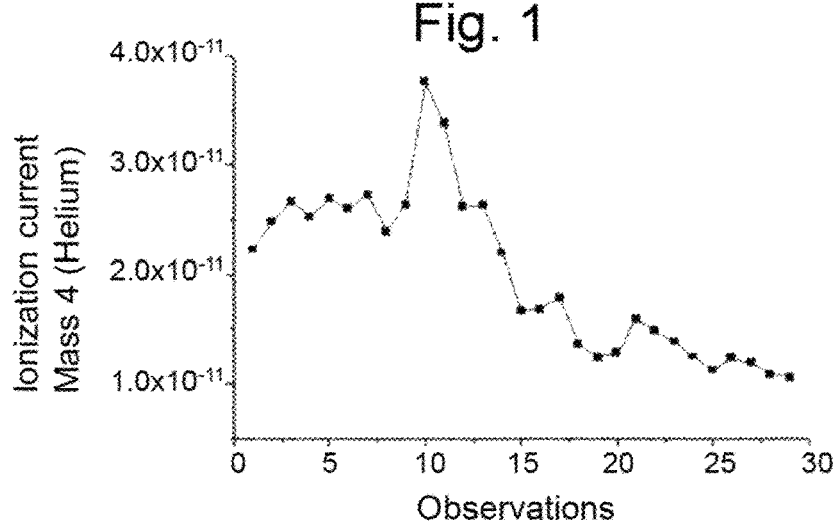
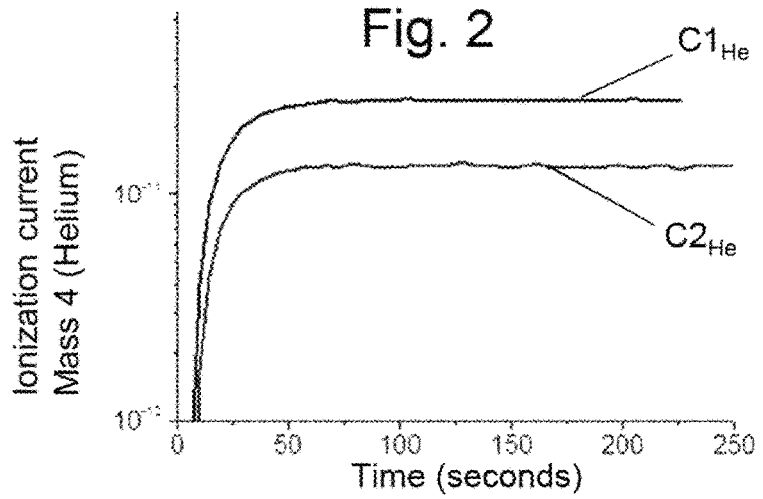
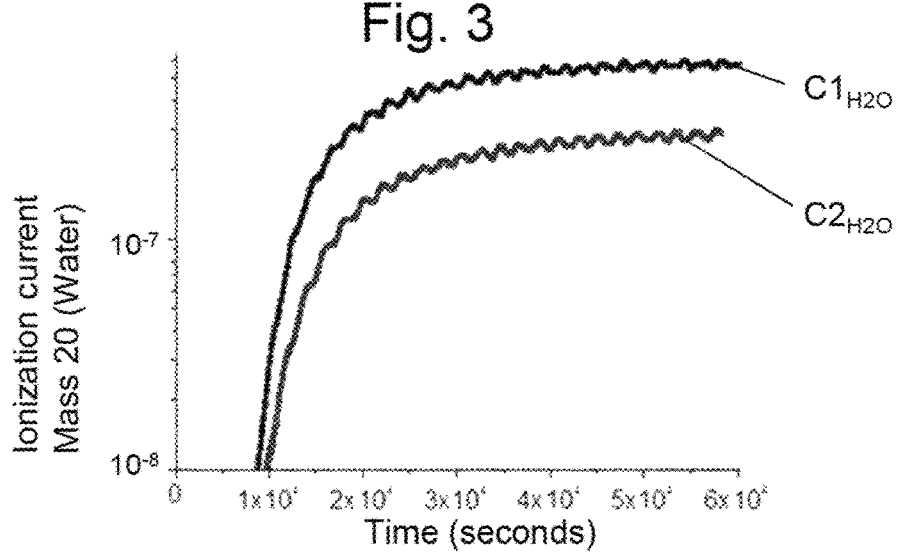

METHOD AND DEVICE FOR MEASURING PERMEATION BY MASS SPECTROMETRY

CROSS REFERENCE TO RELATED APPLICATIONS

This application claims the benefit of the filing date of French Patent Application No. 1461342 filed Nov. 24, 2014, the disclosure of which is hereby incorporated herein by reference.

FIELD OF THE INVENTION

The present invention relates to the field of gas permeation, and more particularly to a device and a method for measuring gas permeation through solid materials.

BACKGROUND OF THE INVENTION

Selection of materials for certain applications, such as packaging or electronics for example, requires study of the permeation of certain gases through these materials. By permeation, is meant the mechanism for letting a gas through a material according to gas absorption steps in the material, by diffusion steps of this gas through the material, and by desorption of the gas on the other side of the material. For example, gas permeation measurements for oxygen or steam (i.e. water vapor), through materials to be selected, are the most widespread.

In the case of materials intended for agro-food packaging for example, the study of the permeation of common gases through the materials, and more particularly oxygen and steam, are critical. The required levels of permeability to these gases are extremely low, and the study of permeation therefore requires devices for measuring permeation having significant sensitivities.

In response to this problem, many devices for measuring permeation have been developed, based on various principles for tracking gases, and each having their drawbacks.

In particular a device for measuring permeation flows has been developed, comprising a measurement enclosure in a high vacuum, the bather film for which permeation is to be studied, is placed at the interface between two chambers. The upstream chamber to the barrier film is filled with a controlled pressure of the targeted gas, for example steam or oxygen. A vacuum is applied to the downstream chamber and coupled with a measurement apparatus capable of detecting the target gas having diffused by permeation through the sample to be tested, such as for example a mass spectrometer. The gas present in the upstream chamber is transmitted into the downstream chamber by a permeation process and measurement of permeation of the film consists in detecting the transmitted flow by the detection means set into place on the downstream side. The detection of the flow consists in measuring an ionization current corresponding to the mass of the target gas. The measurement is then converted into a gas flow transmitted per unit surface J(t) (in $g \cdot m^{-2} \cdot d^{-1}$) by using a reference sample or a reference calibrated leak which generates a controlled flow of target gas.

In order to increase the sensitivity of the measurements conducted with such devices, it was proposed to use, for a gas for which one tries to determine the permeation through the material, an isotope gas of this gas, i.e. having a different mass number. Thus, by for example using a mass spectrometer as an analyzer in the measurement enclosure, it is possible to reduce the detection thresholds of the permeation by several orders of magnitude. Indeed, the natural isotope abundance of these elements being very low, the contamination of the enclosure with these species is all the less significant.

U.S. Pat. No. 6,624,621 describes a device for measuring permeation taking up again the principles mentioned above and which further has the advantage of carrying out permeation measurements for several different gases simultaneously, which gives the possibility of having measurements with good sensitivity and makes the selection of the materials more rapid.

The use of a mass spectrometer as a measurement means is actually well adapted since it allows measurement of a large variety of gases and the use of an isotope as a target gas gives the possibility of accessing great adequate measurement sensitivity for measuring highly barrier-forming materials. A mass spectrometer is an analysis means allowing detection and identification of molecules of interest by measuring their mass. In an enclosure placed in a dynamic vacuum situation, the mass spectrometer allows the measurement of the pressures of the residual gases. In the case of a permeation measurement, the permeation flow of the sample will be expressed by an increase in the residual pressure of the target gas up to a stabilized value which is the permeation value. The signal from the mass spectrometer corresponds to the ionization current (optionally amplified) of the masses of interest corresponding to the target gas for which one tries to determine the permeation through the sample. For example, the mass 4 will be measured for helium, the mass 18 for water or further the mass 20 for heavy water.

However, it was ascertained that the ionization current of the mass spectrometer for a given mass may vary over time without this corresponding to an actual variation of the partial pressure in the enclosure. This observation was established by conducting permeation measurements to helium gas with a reference material (for example a polyester film stored under controlled conditions). The measurement then corresponds to the ionization current of the mass 4 in the stabilized condition of permeation. FIG. 1 shows a set of such measurements conducted under strictly identical conditions (temperature, upstream helium pressure, reference sample). In FIG. 1, is illustrated the control card for the measurement of permeation to helium of the reference material. A significant variability of the ionization current among the different measurements is seen while the latter should be identical.

This variability forces a systematic control on the reference before any series of measurements in order to calibrate the apparatus and to be able to compare the measurements with each other. These steps for calibrations are made before and/or after the measurement of permeation on the sample to be tested. For example it is possible to use a reference film or to use calibrated leaks which deliver a controlled amount of target gas in the measurement enclosure and thus allow calibration of the mass spectrometer. Patent application US 2010/0223979 gives an example of a method wherein calibration is carried out before permeation measurements as such, this calibration may for example be conducted with a flow of a mixture of gases in which the target gas is highly diluted, i.e. present in a very small amount. These calibration steps are however a problem since they will significantly extend the durations of the permeation measurements which already are very long. Further, they are not totally satisfactory since they do not allow fine correction of the different modifications of the signal from the mass spectrometer which may occur during the permeation measurement.

An object of the present invention is therefore to propose an improved method for measuring permeation and an associated device which give the possibility of solving at least one of the aforementioned drawbacks.

More particularly, an object of the present invention is to propose an improved method for measuring permeation and an associated device, which give the possibility of providing reliable and accurate permeation measurements, while not extending the usual measurement times.

SUMMARY OF THE INVENTION

To this end is proposed a method for measuring gas permeation through a material (M) arranged in a permeation enclosure comprising a first chamber and a second chamber, the first chamber being separated from the second chamber by the material (M), and the second chamber being in fluidic communication with a measurement enclosure, the method comprising the following steps (a)-(d) illustrated in FIG. 5:
  a) Supplying gas to the permeation enclosure during which the first chamber is supplied with a target gas flow comprising at least one target gas corresponding to a gas for which one tries to determine the permeation through the material (M), and simultaneously supplying gas to the measurement enclosure with at least one calibrated flow comprising at least one reference gas, the reference gas being different from the target gas;
  b) during the step of supplying gas, measuring in the measurement enclosure the reference gas present at an instant (t) and the target gas present at the same instant (t) stemming from the second chamber after having passed through the material (M) by permeation;
  c) calculating a correction factor at instant (t) by comparing the measurement of the reference gas present at instant (t) with the calibrated flow of reference gas; and
  d) determining the permeation of the material (M) to said gas, from the measurement of the target gas present at instant (t) corrected by the correction factor at instant (t).

Preferred but non-limiting aspects of this method, taken alone or in combination, are the following:
  the steps b) and c) of respectively measuring the gases present in the measurement enclosure and of calculating the correction factor are carried out several times overtime during step a) of supplying gas, said step d) of calculating the permeation of the material (M) to the gas being carried out from different measurements of the target gas overtime, each measurement of the target gas being corrected by the corresponding correction factor.
  the reference gas is a neutral gas towards the target gas.
  the calibrated flow of reference gas comprises several different reference gases, wherein step b) comprises the simultaneous measurement of the different reference gases present in the measurement enclosure at instant (t), and wherein in step c) several correction factors are calculated at instant (t) from the comparison of the measurement of each reference gas present at instant (t) with the calibrated flow of the corresponding reference gas.
  in step d), one selects the correction factor corresponding to the reference gas for which the measurement at instant (t) is the closet in intensity to the measurement of the target gas present at instant (t).
  the target gas flow comprises several different target gases, corresponding to several gases for which one tries to determine the permeation through the material (M), said step b) comprising the simultaneous measurement of different target gases present in the measurement enclosure at instant (t).
  the calibrated flow of reference gas comprises at least one gas selected from argon (Ar), nitrogen (N), krypton (Kr), and neon (Ne).
  the target gas flow comprises at least one isotope gas of the gas for which one tries to determine the permeation through the material (M).
  the target gas flow comprises at least one gas selected from among:
    helium (He);
    oxygen ($O_2$);
    deuterium oxide ($D_2O$) for measuring permeation to steam (i.e. water vapor);
    the isotope ($D_2{}^{18}O_2$) of deuterium oxide for measuring the permeation to steam (i.e. water vapor);
    oxygen 18 ($^{18}O_2$) for measuring the permeation of the material (M) to oxygen ($O_2$);
    oxygen 17 ($^{17}O_2$) for measuring the permeation of the material (M) to oxygen ($O_2$);
    or a combination thereof.
  in step b), a mass spectrometer is used for measuring the gases present in the measurement enclosure, the mass spectrometer delivering for each detected gas having a different mass, a measurement signal as an ionization current, the value of the ionization current for the reference gas being used for correcting the value of the ionization current of the other detected gases by comparison with the value of the reference gas calibrated flow.
  the method is used for measuring permeation to steam (i.e. water vapor).

A device for measuring permeation specially adapted for applying this method for measuring permeation is also proposed.

In particular, a device for measuring permeation of gases through a material is proposed for applying the proposed method, comprising:
  A permeation enclosure having a first chamber and a second chamber separated by the material,
  a measurement enclosure in fluidic communication with the second chamber and an analyzer for analyzing the gases present in the measurement enclosure stemming from the second chamber after having passed through the material by permeation,
characterized in that it further comprises at least one line for supplying gas coupled with a reference gas source on the one hand and with the measurement enclosure on the other hand for continuously supplying said measurement enclosure with the reference gas flow.

According to a preferred but non-limiting aspect of this device, the supply line further comprises a valve positioned between the reference gas source and the measurement enclosure, the valve being configured for regulating the reference gas flow entering the measurement enclosure.

BRIEF DESCRIPTION OF THE DRAWINGS

Other features and advantages of the invention will further become apparent from the description which follows, which is purely illustrative and non-limiting and should be read with reference to the appended drawings, wherein:

FIG. 1, already commented, is a graphic illustration of a card for controlling the helium measurement of a reference sample with a mass spectrometer of a measurement device of the prior art;

FIG. 2 is a graphic illustration illustrating the ionization current of mass 4 (helium) for two measurements successively taken on a same polyester film;

FIG. 3 is a graphic illustration illustrating the ionization current of mass 20 (water) for two measurements successively taken on a same polyester film;

DETAILED DESCRIPTION

Figure 4:
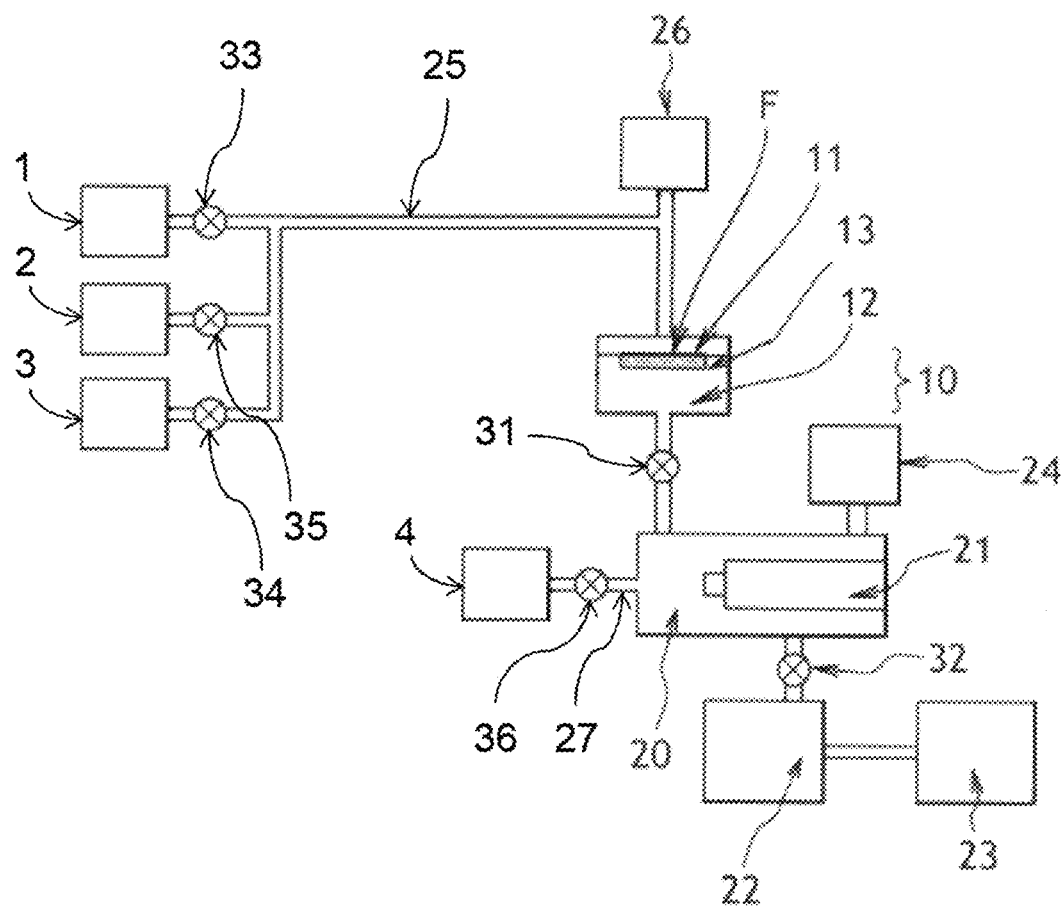
FIG. 4 is a block diagram illustrating the device for measuring permeation according to the invention.
Figure 5:
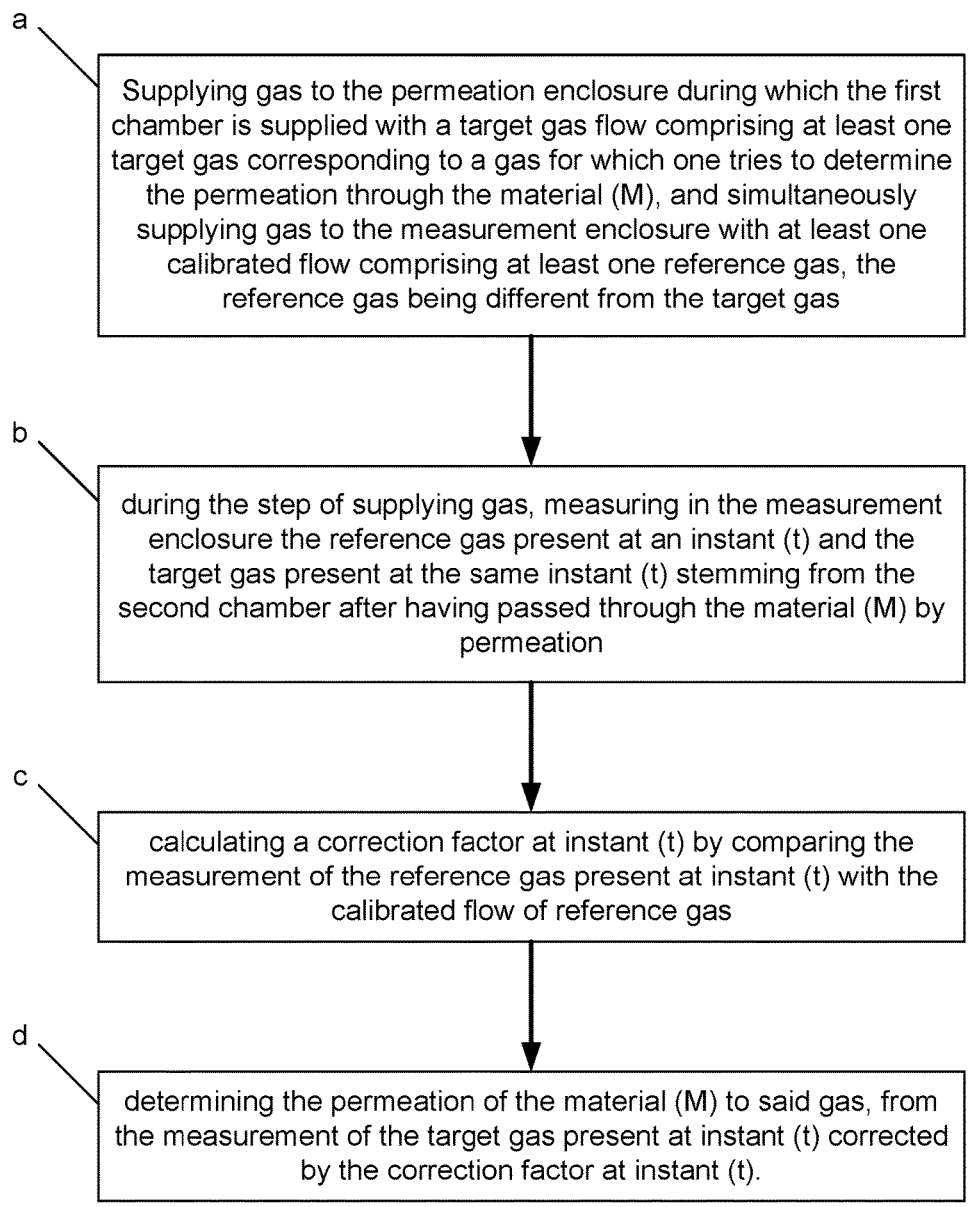
FIG. 5 is a block diagram illustrating a method for measuring gas permeation through a material according to the invention.

The inventors discovered surprisingly that the measurement variability of a mass spectrometer, for a same partial pressure, does not depend in proportion, on the measured mass.

Several permeation measurements were actually conducted on a same film of polyester, the results of which are illustrated in the curves of FIGS. 2 and 3.

More specifically, a first measurement of permeation to helium (He) was first conducted on the polyester film with a conventional permeation device using a mass spectrometer, like for example the one described in U.S. Pat. No. 6,624,621. The results of this measurement are illustrated on curve $C1_{He}$ of FIG. 2 which illustrates the time-dependent change in the ionization current of the mass 4 over time. This first measurement of permeation to helium was immediately followed by a first measurement of permeation to water ($H_2O$), the results of this measurement being illustrated on curve $C1_{H2O}$ of FIG. 3 which illustrates the change in the ionization current of mass 20 over time.

A second measurement of permeation to helium (He) and then a second measurement of permeation to water ($H_2O$) were then conducted, the results of these measurements being respectively illustrated on curve $C2_{He}$ of FIG. 2 and on curve $C2_{H2O}$ of FIG. 3.

Table 1 below indicates the value of the ionization current under stabilized conditions for each of the measurements described above:

TABLE 1

|  | Helium (in A/mbar) | Water (in A) [at 38° C., with 90% of relative humidity (RH)] |
| --- | --- | --- |
| Measurement 1 (M1) | 2.62E−11 | 5.86E−07 |
| Measurement 2 (M2) | 1.34E−11 | 2.89E−07 |
| Difference M2/M1 | −49% | −51% |

It is observed that the drops in the ionization currents measured between the first and the second measurement are substantially the same for helium and for water. This confirms that the measurement variability of a mass spectrometer, for a same partial pressure, does not depend, in proportion, on the measured mass.

Thus, according to the invention, during the permeation measurements the use of a calibrated leak of a reference gas is proposed and the measurement of this gas in a continuous way at the same time as the permeation measurement of the target gas of the sample is proposed.

Such a calibrated leak of a reference gas is preferably directly connected in the measurement chamber where a gas analyzer is used for analyzing the gases having crossed the sample by permeation, this analyzer being preferably a mass spectrometer.

The variations ascertained by the analyzer on the measurement of the calibrated leak which by definition is constant, are therefore related to the variability observed during the use of this type of apparatus.

Thus a correction factor may easily be calculated and passed on to the measurement of permeation of the target gas, so as to have a measurement of permeation of the target gas wherein the fluctuations due to the measurement apparatus are neutralized.

For the permeation measurements, a target gas is used corresponding to a gas for which one tries to determine the permeation through the material (M). Thus, it is possible to use as a target gas the specific gas for which one tries to determine the permeation through the material (M). Preferably, the target gas used is an isotope gas of the gas for which one tries to determine the permeation through the material (M), i.e. a species having a different mass number. Thus, by for example using a mass spectrometer as an analyzer in the measurement enclosure, it is possible to reduce the detection thresholds of the permeation by several orders of magnitude. Indeed, the natural isotope abundance of these elements is very low, the pollution of the chamber by these species is all the less important.

Preferably, the reference gas used for the calibrated gas flow used is a gas which is neutral towards the target gas(es) selected. A neutral gas towards a target gas is defined as a gas for which the presence with said target gas will not influence the measurement of said target gas.

Preferably, a neutral gas is used which will not generate in the measurement enclosure, during ionization by the mass spectrometer, a mass corresponding to the mass of the selected target gas(es).

As a reference gas, for example it is possible to use a flow of argon (Ar), of nitrogen (N), of krypton (Kr), and/or of neon (Ne).

Argon (Ar), nitrogen (N), krypton (Kr), and/or neon (Ne) are actually particularly advantageous since they behave like neutral gases towards most of the target gases which are generally measured, in particular towards helium (He), oxygen ($O_2$) and/or deuterium oxide ($D_2O$) for measuring permeation to steam (i.e. water vapor). They also behave like a neutral gas when oxygen 18 ($^{18}O_2$) and/or oxygen 17 ($^{17}O_2$) are used as an isotope gas for measuring the permeation of the material (M) to oxygen ($O_2$), or further towards an isotope of deuterium oxide such as the heavy isotope ($D_2{}^{18}O_2$).

The use of a calibrated neutral gas leak gives the possibility of correcting the inherent variability during the use of a mass spectrometer with the following additional advantages.

The reference gas calibrated flow is continuously measured during the whole measurement of permeation of the gas. Thus, this allows real time correction of the permeation measurement, which is particularly advantageous in permeation measurements which last for a long time, such as for example the measurements of permeation to water which may last for several weeks, and for which a one-off calibration before or after the measurement is generally not sufficient.

Moreover, the use of this calibrated neutral gas leak gives the possibility of avoiding the resort to calibrations using a target gas calibrated leak (limited to an initial calibration for having an absolute measurement of the target gas), which limits the pollution of the measurement enclosure with the target gas and is thus favorable to the detection sensitivity.

Indeed, the initial background noise in the measurement enclosure is thus strongly reduced or even totally suppressed.

This also simplifies the measurement procedures since a target gas calibrated leak has to be managed by a set of valves and associated procedures and cannot be permanently put into contact with the mass spectrometer since this would exaggeratedly perturb the measurement and would considerably limit the measurement sensitivity.

Finally, the use of a calibrated neutral gas leak allows calibration for gases like water for which no simple calibration solution existed. Indeed, for water, the calibration is generally accomplished by measuring a reference material with a known permeation to water (a measurement which at least lasts for several hours without taking into account the periods for setting into place the sample and the water atmosphere). The use of a permanent calibrated neutral gas leak during the measurement gives the possibility of getting rid of any particular calibration to water.

According to a preferred embodiment, several different reference gases are used simultaneously, the flow of which is calibrated at the inlet of the measurement enclosure.

Thus, a correction factor may be applied, different to the signal of the target gas depending on the intensity of the latter. The selected correction factor is preferably the one defined by the measurement of the calibrated leak which is the closest in intensity (ionization current) to the measurement of the target gas at the moment of the correction.

The use of calibrated leaks with different intensities gives the possibility of controlling the possible variations of the spectrometer on the whole of the measurement range. It is thus possible to control the linearity of the signal over the whole of the measurement range.

The reference gases used are neutral relatively to the target gas(es) and are also neutral with respect to each other (according to the definition of neutrality as specified above).

A preferred embodiment means for the use of several reference leaks is the use of a single leak (i.e. a single tank) containing several gases with a leak intensity of each gas determined by the respective partial pressures of the gases in the tank of the leak. This latter means gives the possibility of simplifying the mounting by using a single tank for the neutral leak.

Another means for covering the widest possible spectrum in terms of intensity for a neutral leak is the use of a device for varying the flow at the output of a leak (for example a valve which may be controlled) which gives the possibility of varying the intensity of the leak. In the latter case, the measurement will be a one-off measurement because of the time required for stabilizing the leak for each relevant flow rate.

A permeameter which may be used for applying the presented method for measuring permeation is illustrated in FIG. 4. The process for permeation of a gas through a material M is based on the differences of partial pressures of this gas, also called a permeating gas, on either side of the material M, generally sampled as a film F.

The permeameter comprises a permeation enclosure 10 which comprises a first chamber 11 and a second chamber 12 separated by the film F of material M. For studying the differences in partial pressures of the permeating gas between the first chamber 11, located upstream in the device, and the second chamber 12, located downstream in the device, it is important to ensure zero or negligible downstream partial pressure, relatively to the upstream pressure. A controlled atmosphere, with an upstream pressure determined in permeating gas(es), is produced above the film to be tested. Below the film, the second chamber 12, in which a high vacuum is maintained, gives the possibility of ensuring the zero, or negligible downstream pressure condition, towards the upstream pressure.

In order to avoid excessive deformation of the film F, the permeation enclosure 10 preferably comprises a supporting means 13, such as a porous metal frit. The film F thus rests on this supporting means 13 which is positioned between the first chamber 11 and the second chamber 12, and is formed so as to allow transmission of the gases.

Downstream from the film F, connected to the second chamber 12, an analysis means is provided, adapted for tracking the downstream partial pressure of permeating gas(es). The analysis means of the measurement device comprises a measurement chamber 20 in fluidic communication with the second chamber 12. Preferably, the measurement enclosure 20 is connected to the second chamber 12 via a valve 31 giving the possibility of isolating, if required, the measurement chamber 20 from the second chamber 12. This measurement enclosure 20 is set in vacuo by a pumping system comprising a primary pump 23 and a secondary pump 22, which are preferentially placed in series relatively to each other. The measurement enclosure and the pumping system are connected via a valve 32.

Further, the analysis means comprises an analyzer 21 of residual gases placed in the measurement enclosure 20 in vacuo, and positioned so as to be able to analyze with the best sensitivity as possible the gases stemming from the second chamber 12 before being sucked up by the pumps 22 and 23. The analyzer 21 may for example a mass spectrometer placed in a measurement enclosure 20 evacuated by a dry primary pump 23 and a turbo pump 22 placed in series. For better sensitivity, the spectrometer is positioned on the path of the gas flow between the second chamber 12 and the pumps 22 and 23. A pressure gauge 24 may also be provided for measuring the total pressure prevailing within the measurement enclosure 20.

The mass spectrometer 21 used can only operate at low pressures and therefore requires a measurement enclosure 20 with a secondary vacuum (of the order of $10^{-4}$ torrs at most). Consequently, the measurement enclosure 20 is permanently pumped with the pumps 22 and 23 during the transfer of the gases by permeation through the sample film F. Thus, the partial pressure of each of the gases having crossed the sample increases until it stabilizes when the permeation flow becomes equal to the pumped flow. The mass spectrometer 21 delivers a signal which is a current resulting from the ionization of the atoms of a measured species, which is proportional to the partial pressure of this species. This signal is called the ionization current. As the pumping is efficient and the permeation of the samples is low, the stabilization pressure is also very low so that it may be considered that the pressure on the downstream face of the sample film F remains quasi zero over time. The flow of a permeating agent through the sample film F is therefore proportional to the partial pressure of the permeating agent tracked when the permanent conditions are attained. For extremely low permeation flows, closing the valve 32 will allow a cumulative measurement in the total pressure limit set by the analysis means 21 i.e. of the order of $10^{-4}$ torrs which will give the possibility of observing the criterion of negligible downstream pressure with respect to the upstream pressure.

From the thereby calculated permeation flow, it is possible to infer therefrom the permeability of the material M to the relevant gas by considering the thickness e of the sample film F.

The gas supply means of the measurement device comprises a main gas supply line 25 via which a target gas flow may be injected into the first chamber 11 of the permeation enclosure 10. The flow of target gas comprises one or several gases for which one tries to measure the permeation through the material M.

For example it may be provided that the supply line be coupled with several gas sources (1; 2; 3) via valves (33; 34; 35) giving the possibility of selecting the gases to be injected into the target gas flow.

The measurement of the pressure injected into the target gas is generally made with a means for controlling pressure 26 directly placed on the first chamber of the permeation enclosure 10.

The proposed permeation device has the particularity of having an additional gas supply line (27) which allows continuous injection of a flow of reference gas into the measurement enclosure (20).

This additional gas supply line (27) is therefore coupled with a source (4) of reference gas on the one hand, and with the measurement enclosure (20) on the other hand for continuously supplying said measurement enclosure (20) with the reference gas flow.

According to a particular embodiment, the additional gas supply line (27) further comprises a valve (36) allowing regulation of the flow rate of the reference gas flow entering the measurement enclosure (20). Such a valve (36) is optional but may be particularly advantageous when it is desired to generate several flows with different flow rates from the same reference gas.

It is possible to couple the additional gas supply line (27) directly on the second chamber (12) of the permeation enclosure (10), but it is preferable to directly couple it on the measurement enclosure (20) as described above since this gives the possibility of being able to properly isolate the second chamber (12), notably during possible purges, and the time for balancing the measurement of the reference gas with the analyzer (21) is also accelerated when the additional gas supply line (27) is directly connected onto the measurement enclosure (20).

It should be noted that the proposed configuration for the permeameter is not limiting and that other arrangements may be contemplated. In particular, provision may be made for several additional gas supply lines connected to the measurement enclosure (20) so as to be able to generate several different calibrated leaks.

The invention claimed is:

1. A method for measuring gas permeation through a material (M) arranged in a permeation enclosure comprising a first chamber and a second chamber, the first chamber being separated from the second chamber by the material (M), and the second chamber being in fluidic communication with a measurement enclosure, the method comprising the following steps:
   a) Supplying gas to the permeation enclosure during which the first chamber is supplied with a target gas flow comprising at least one target gas corresponding to a gas for which one tries to determine the permeation through the material (M), and simultaneously supplying gas to the measurement enclosure with at least one calibrated flow comprising at least one reference gas, the reference gas being different from the target gas;
   b) during the step of supplying gas, measuring in the measurement enclosure the reference gas present at an instant (t) and the target gas present at the same instant (t) stemming from the second chamber after having passed through the material (M) by permeation;
   c) calculating a correction factor at instant (t) by comparing the measurement (M2) of the reference gas present at instant (t) with a measurement (M1) of the reference gas at an earlier time; and
   d) determining the permeation of the material (M) to said gas, from the measurement of the target gas present at instant (t) corrected by the correction factor at instant (t).

2. The method of claim 1, wherein the steps b) and c) of measuring the gases present in the measurement enclosure and of calculating the correction factor are carried out several times overtime during step a) of supplying gas, said step d) of calculating the permeation of the material (M) to the gas being carried out from different measurements of the target gas overtime, each measurement of the target gas being corrected by the corresponding correction factor.

3. The method of claim 1, wherein the reference gas is a neutral gas towards the target gas.

4. The method of claim 1, wherein the target gas flow comprises several different target gases, corresponding to several gases for which one tries to determine the permeation through the material (M), step b) comprising the simultaneous measurement of different target gases present in the measurement enclosure at instant (t).

5. The method of claim 1, wherein the calibrated flow of reference gas comprises at least one gas selected from argon (Ar), nitrogen (N), krypton (Kr), and neon (Ne).

6. The method of claim 1, wherein the target gas flow comprises at least one isotope gas of the gas for which one tries to determine the permeation through the material (M).

7. The method of claim 1, wherein the target gas flow comprises at least one gas selected from among:
   helium (He);
   oxygen ($O_2$);
   deuterium oxide ($D_2O$) for measuring permeation to steam;
   the isotope ($D_2{}^{18}O_2$) of deuterium oxide for measuring the permeation to steam;
   oxygen 18 ($^{18}O_2$) for measuring the permeation of the material (M) to oxygen ($O_2$);
   oxygen 17 ($^{17}O_2$) for measuring the permeation of the material (M) to oxygen ($O_2$);
   or a combination thereof.

8. The method of claim 1, wherein in step b), a mass spectrometer is used for measuring the gases present in the measurement enclosure, the mass spectrometer delivering for each detected gas having a different mass, a measurement signal as an ionization current, the value of the ionization current for the reference gas being used for correcting the value of the ionization current of the other detected gases by comparison with the value of the reference gas calibrated flow.

9. The method of claim 1, wherein the reference gas is supplied to the measurement enclosure without having to pass through the material (M) by permeation.

10. A method for measuring gas permeation through a material (M) arranged in a permeation enclosure comprising a first chamber and a second chamber, the first chamber being separated from the second chamber by the material (M), and the second chamber being in fluidic communication with a measurement enclosure, the method comprising the following steps:
   a) Supplying gas to the permeation enclosure during which the first chamber is supplied with a target gas flow comprising at least one target gas corresponding to a gas for which one tries to determine the permeation through the material (M), and simultaneously supplying gas to the measurement enclosure with at least one calibrated flow comprising several different reference gases, the reference gases being different from the target gas;

b) during the step of supplying gas, measuring simultaneously in the measurement enclosure the different reference gases present at an instant (t) and the target gas present at the same instant (t) stemming from the second chamber after having passed through the material (M) by permeation;

c) calculating several correction factors at instant (t), each correction factor at instant (t) being calculated by comparing the measurement (M2) of one of the different reference gases present at instant (t) with a measurement (M1) of such reference gas at an earlier time; and d) determining the permeation of the material (M) to said gas, from the measurement of the target gas present at instant (t) corrected by at least one of the correction factors at instant (t).

11. The method of claim 10, wherein in step d), one selects the correction factor corresponding to the reference gas for which the measurement at instant (t) is the closet in intensity to the measurement of the target gas present at instant (t).

12. The method of claim 10, wherein the target gas flow comprises several different target gases, corresponding to several gases for which one tries to determine the permeation through the material (M), step b) comprising the simultaneous measurement of different target gases present in the measurement enclosure at instant (t).

13. The method of claim 10, wherein the calibrated flow of reference gases comprises at least one gas selected from argon (Ar), nitrogen (N), krypton (Kr), and neon (Ne).

14. The method of claim 10, wherein the target gas flow comprises at least one isotope gas of the gas for which one tries to determine the permeation through the material (M).

15. The method of claim 10, wherein the target gas flow comprises at least one gas selected from among:
helium (He);
oxygen ($O_2$);
deuterium oxide ($D_2O$) for measuring permeation to water vapor;
the isotope ($D_2{}^{18}O_2$) of deuterium oxide for measuring the permeation to water vapor;
oxygen 18 ($^{18}O_2$) for measuring the permeation of the material (M) to oxygen ($O_2$);
oxygen 17 ($^{17}O_2$) for measuring the permeation of the material (M) to oxygen ($O_2$);
or a combination thereof.

16. The method of claim 10, wherein in step b), a mass spectrometer is used for measuring the gases present in the measurement enclosure, the mass spectrometer delivering for each detected gas having a different mass, a measurement signal as an ionization current, the value of the ionization current for the reference gas being used for correcting the value of the ionization current of the other detected gases by comparison with the value of the reference gas calibrated flow.

17. A method for measuring permeation of water vapor through a material (M) arranged in a permeation enclosure comprising a first chamber and a second chamber, the first chamber being separated from the second chamber by the material (M), and the second chamber being in fluidic communication with a measurement enclosure, the method comprising the following steps:

a) Supplying gas to the permeation enclosure during which the first chamber is supplied with a target gas flow comprising at least one target gas corresponding to water vapor, and simultaneously supplying gas to the measurement enclosure with at least one calibrated flow comprising at least one reference gas, the reference gas being different from the target gas;

b) during the step of supplying gas, measuring in the measurement enclosure the reference gas present at an instant (t) and the target gas present at the same instant (t) stemming from the second chamber after having passed through the material (M) by permeation;

c) calculating a correction factor at instant (t) by comparing the measurement (M2) of the reference gas present at instant (t) with a measurement (M1) of the reference gas at an earlier time; and d) determining the permeation of the material (M) to said gas, from the measurement of the target gas present at instant (t) corrected by the correction factor at instant (t).

18. The method of claim 17, wherein the target gas flow comprises at least one gas selected from among:
the deuterium oxide ($D_2O$);
the isotope ($D_2{}^{18}O_2$) of deuterium oxide;
or a combination thereof.

* * * * *